United States Patent [19]
Palker et al.

[11] Patent Number: 5,516,632
[45] Date of Patent: May 14, 1996

[54] SYNTHETIC PEPTIDES

[75] Inventors: Thomas J. Palker; Barton F. Haynes, both of Durham, N.C.

[73] Assignee: Duke University, Durham, N.C.

[21] Appl. No.: 116,733

[22] Filed: Sep. 7, 1993

Related U.S. Application Data

[63] Continuation of Ser. No. 771,553, Oct. 8, 1991, abandoned, which is a continuation-in-part of Ser. No. 741,226, Aug. 5, 1991, abandoned, which is a continuation of Ser. No. 303,436, Jan. 30, 1989, abandoned, which is a continuation-in-part of Ser. No. 153,420, Feb. 8, 1988, abandoned.

[51] Int. Cl.$^6$ .............. C12Q 1/70; C07K 7/08; A61K 38/10; A61K 39/21
[52] U.S. Cl. .......... 435/5; 424/188.1; 530/324; 530/325; 530/326; 530/327; 530/328; 530/329; 514/12; 514/13; 514/14; 514/15; 514/16; 514/17
[58] Field of Search .............. 514/12–17; 500/324–329; 424/188.1; 435/7.1, 5

[56] References Cited

U.S. PATENT DOCUMENTS

| | | | |
|---|---|---|---|
| 4,525,300 | 6/1985 | Yoshida et al. | 530/327 |
| 4,663,436 | 5/1987 | Elder et al. | 530/326 |
| 4,689,398 | 8/1987 | Wu et al. | 530/327 |
| 4,724,258 | 2/1988 | Yoshida et al. | 530/350 |
| 4,822,606 | 4/1989 | Snyderman et al. | 530/350 |
| 4,833,071 | 5/1989 | Wang et al. | 435/7 |
| 4,879,212 | 11/1989 | Wang et al. | 530/324 |
| 5,066,579 | 11/1991 | Reyes | 435/5 |

FOREIGN PATENT DOCUMENTS 2209889  8/1990  Japan.

OTHER PUBLICATIONS

Palker et al, "Mapping of Homologous, Amino–Terminal Neutralizing Regions of Human T–Cell Lymphotropic Virus Type I and II gp46 Envelope Glycoproteins", Journal of Virology 66(10):5879–5889 (1992).

Ralston et al, "Identification and Synthesis of the Epitope for a Human Monoclonal Antibody Which Can Neutralize Human T–cell Leukemia/Lymphotrophic Virus TypeI*", The Journal of Biological Chemistry, vol. 284, No. 28, pp. 16343–16346 (1989).

Lipka et al, "Determination of a Unique and Immunodominant Epitope of Human T Cell Lymphotrophic Virus Type I", The Journal of Infectious Diseses, 162:353–357 (1990).

Kiyokawa et al, PNAS USA 81:6202 (1984).
Kurata et al J. of Immunol. 143:2024 (1989).
Tanaka J. of Immunol. 147:354 (1991).
Nakamura Int. J. Cancer 40:403 (1987).

Primary Examiner—Michael P. Woodward
Attorney, Agent, or Firm—Nixon & Vanderhye

[57] ABSTRACT

The present invention relates to immunogenic preparations of peptides comprising amino acid sequences corresponding to antigenic determinants of the envelope glycoprotein of HTLV-I or HTLV-II covalently coupled, directly or through a spacer molecule, to carrier molecules suitable for vaccination of mammals. The invention also relates to the use of such peptides in diagnostic assays.

26 Claims, 7 Drawing Sheets

FIG. 6A

Bar chart: No. of Syncytia (HTLV-I) vs Amino Acids Changed to Alanine (W, T, K, K, P, N, R, N, G, G, G)

FIG. 6B

Bar chart: No. of Syncytia (HTLV-I) vs Amino Acids Changed to Alanine (W, T, K, K, P, N, R, N, G, G, G)

FIG. 6C

Bar chart: No. of Syncytia (HTLV-I) vs Amino Acids Changed to Alanine (W, T, K, K, P, N, R, N, G, G, G)

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
           ( A ) LENGTH: 11 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:1:

Trp  Thr  Lys  Lys  Pro  Asn  Arg  Asn  Gly  Gly  Gly
   1                  5                        10

( 2 ) INFORMATION FOR SEQ ID NO:2:

( i ) SEQUENCE CHARACTERISTICS:
           ( A ) LENGTH: 15 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:2:

Val  Ser  Ser  Tyr  His  Ser  Lys  Pro  Cys  Asn  Pro  Ala  Gln  Pro  Val
   1                  5                        10                       15

( 2 ) INFORMATION FOR SEQ ID NO:3:

( i ) SEQUENCE CHARACTERISTICS:
           ( A ) LENGTH: 23 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:3:

Cys  Pro  His  Trp  Thr  Lys  Lys  Pro  Asn  Arg  Asn  Gly  Gly  Gly  Tyr  Tyr
   1                  5                        10                       15

Ser  Ala  Ser  Tyr  Ser  Asp  Pro
                  20

( 2 ) INFORMATION FOR SEQ ID NO:4:

( i ) SEQUENCE CHARACTERISTICS:
           ( A ) LENGTH: 16 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:4:

Cys  Leu  Asn  Thr  Glu  Pro  Ser  Gln  Leu  Pro  Pro  Thr  Ala  Pro  Pro  Tyr
   1                  5                        10                       15

( 2 ) INFORMATION FOR SEQ ID NO:5:

( i ) SEQUENCE CHARACTERISTICS:
           ( A ) LENGTH: 22 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:5:

```
Ser  Ser  Pro  Tyr  Trp  Lys  Phe  Gln  His  Asp  Val  Asn  Phe  Thr  Gln  Glu
1              5                        10                       15

Val  Ser  Arg  Leu  Asn  Cys
                    20
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Cys  Leu  Leu  Pro  His  Ser  Asn  Leu  Asp  His  Ile  Leu  Glu  Pro  Ser  Ile
1              5                        10                       15

Pro  Trp  Lys  Ser  Lys  Tyr
                    20
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Tyr  Leu  Pro  Phe  Asn  Trp  Thr  His  Cys  Phe  Asp  Pro  Gln  Cys
1              5                        10
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Cys  Pro  Pro  Phe  Ser  Leu  Ser  Pro  Val  Pro  Thr  Leu  Gly  Ser  Arg  Ser
1              5                        10                       15

Arg  Arg
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Tyr  Ala  Ala  Gln  Asn  Arg  Arg  Gly  Leu  Asp  Leu  Leu  Phe  Trp  Glu  Gln
1              5                        10                       15

Gly  Gly  Leu  Cys
                20
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Cys Arg Phe Pro Asn Ile Thr Asn Ser His Val Pro Ile Leu Gln Glu
1               5                   10                  15
```

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Cys Pro Ile Leu Gln Glu Arg Pro Pro Leu Glu Asn Arg
1               5                   10
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Cys Ile Leu Arg Gln Leu Arg His Leu Pro Ser Arg Val Arg Tyr Pro
1               5                   10                  15
His Tyr Ser
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Cys Arg Tyr Pro His Tyr Ser Leu Ile Lys Pro Glu Ser Ser Leu
1               5                   10                  15
```

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Pro His Trp Ile Lys Lys Pro Asn Arg Gln Gly Leu Gly Tyr Tyr Ser
1               5                   10                  15
Cys
```

( 2 ) INFORMATION FOR SEQ ID NO:15:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:15:

Ser Ser Tyr His Ser Ser Pro Cys Ser Pro Thr Gln Pro Val Cys
1               5                   10                  15

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Cys Thr Trp Asn Leu Asp Leu Asn Ser Leu Thr Thr Asp Gln Arg Leu
1               5                   10                  15

His Pro Pro Cys
            20

( 2 ) INFORMATION FOR SEQ ID NO:17:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

His Trp Ile Lys Lys Pro Asn Arg Gln Gly Leu Gly Tyr Tyr Ser Pro
1               5                   10                  15

Ser Tyr Asn Asp Pro Cys
            20

( 2 ) INFORMATION FOR SEQ ID NO:18:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Cys Ser Ser Pro Ser Trp Lys Phe His Ser Asp Val Asn Phe Thr Gln
1               5                   10                  15

Glu ( 2 ) INFORMATION FOR SEQ ID NO:19:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Cys Ser Glu Pro Thr Gln Pro Pro Pro Thr Ser Pro Pro Leu Val His
1               5                   10                  15

Asp Ser Asp Leu Glu His
                20

( 2 ) INFORMATION FOR SEQ ID NO:20:

( i ) SEQUENCE CHARACTERISTICS:
         ( A ) LENGTH: 15 amino acids
         ( B ) TYPE: amino acid
         ( D ) TOPOLOGY: linear ( i i ) MOLECULE TYPE: peptide ( x i ) SEQUENCE DESCRIPTION: SEQ ID NO:20:

Cys Ser Leu Ala Pro Val Pro Pro Pro Ala Thr Arg Arg Arg Arg
1               5                   10                  15

( 2 ) INFORMATION FOR SEQ ID NO:21:

( i ) SEQUENCE CHARACTERISTICS:
         ( A ) LENGTH: 16 amino acids
         ( B ) TYPE: amino acid
         ( D ) TOPOLOGY: linear ( i i ) MOLECULE TYPE: peptide ( x i ) SEQUENCE DESCRIPTION: SEQ ID NO:21:

Leu His Glu Val Asp Lys Asp Ile Ser Gln Leu Thr Gln Ile Val Lys
1               5                   10                  15

( 2 ) INFORMATION FOR SEQ ID NO:22:

( i ) SEQUENCE CHARACTERISTICS:
         ( A ) LENGTH: 11 amino acids
         ( B ) TYPE: amino acid
         ( D ) TOPOLOGY: linear ( i i ) MOLECULE TYPE: peptide ( x i ) SEQUENCE DESCRIPTION: SEQ ID NO:22:

Gln Pro Pro Cys Pro Asn Leu Val Ser Tyr Ser
1               5                   10

( 2 ) INFORMATION FOR SEQ ID NO:23:

( i ) SEQUENCE CHARACTERISTICS:
         ( A ) LENGTH: 17 amino acids
         ( B ) TYPE: amino acid
         ( D ) TOPOLOGY: linear ( i i ) MOLECULE TYPE: peptide ( x i ) SEQUENCE DESCRIPTION: SEQ ID NO:23:

Asp Leu Gln Asp Leu Leu Gln Tyr Leu Cys Ser Ser Leu Val Ala Ser
1               5                   10                  15

Leu ( 2 ) INFORMATION FOR SEQ ID NO:24:

( i ) SEQUENCE CHARACTERISTICS:
         ( A ) LENGTH: 22 amino acids
         ( B ) TYPE: amino acid
         ( D ) TOPOLOGY: linear ( i i ) MOLECULE TYPE: peptide ( x i ) SEQUENCE DESCRIPTION: SEQ ID NO:24:

Lys Asp Ile Ser His Leu Thr Gln Ala Ile Val Lys Asn His Gln Asn
1               5                   10                  15

```
    Ile  Leu  Arg  Val  Ala  Gln
                  20
```

( 2 ) INFORMATION FOR SEQ ID NO:25:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Leu  Pro  Pro  Thr  Ala  Pro  Pro  Leu  Leu  Pro  His  Ser  Asn  Leu  Asp  His
1                  5                       10                      15

Ile  Leu  Glu  Pro  Ser  Ile  Pro  Trp  Lys  Ser  Lys  Trp  Thr  Lys  Lys  Pro
              20                      25                      30

Asn  Arg  Asn  Gly  Gly  Gly
              35
```

( 2 ) INFORMATION FOR SEQ ID NO:26:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Pro  Tyr  Val  Glu  Pro  Thr  Ala  Pro  Gln  Val  Leu
1                  5                       10
```

( 2 ) INFORMATION FOR SEQ ID NO:27:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Pro  Tyr  Val  Glu  Pro  Thr  Thr  Thr  Gln  Cys  Phe
1                  5                       10
```

( 2 ) INFORMATION FOR SEQ ID NO:28:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Pro  His  Trp  Thr  Lys  Lys  Pro  Asn  Arg  Asn  Gly  Gly  Gly  Tyr  Tyr  Ser
1                  5                       10                      15

Ala  Ser  Tyr  Ser  Asp  Pro
              20
```

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

Gly Gly Gly Tyr Tyr Ser Ala Ser Tyr Ser Asp Pro
1               5                   10

( 2 ) INFORMATION FOR SEQ ID NO:30:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:30:

Pro His Trp Thr Lys Lys Pro Asn Arg Asn Gly Gly Gly
1               5                   10

( 2 ) INFORMATION FOR SEQ ID NO:31:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:31:

Ala Thr Lys Lys Pro Asn Arg Asn Gly Gly Gly
1               5                   10

( 2 ) INFORMATION FOR SEQ ID NO:32:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:32:

Trp Ala Lys Lys Pro Asn Arg Asn Gly Gly Gly
1               5                   10

( 2 ) INFORMATION FOR SEQ ID NO:33:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:33:

Trp Thr Ala Lys Pro Asn Arg Asn Gly Gly Gly
1               5                   10

( 2 ) INFORMATION FOR SEQ ID NO:34:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:34:

```
Trp Thr Lys Ala Pro Asn Arg Asn Gly Gly Gly
1               5                   10
```

( 2 ) INFORMATION FOR SEQ ID NO:35:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Trp Thr Lys Lys Ala Asn Arg Asn Gly Gly Gly
1               5                   10
```

( 2 ) INFORMATION FOR SEQ ID NO:36:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Trp Thr Lys Lys Pro Ala Arg Asn Gly Gly Gly
1               5                   10
```

( 2 ) INFORMATION FOR SEQ ID NO:37:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Trp Thr Lys Lys Pro Asn Ala Asn Gly Gly Gly
1               5                   10
```

( 2 ) INFORMATION FOR SEQ ID NO:38:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
Trp Thr Lys Lys Pro Asn Arg Ala Gly Gly Gly
1               5                   10
```

( 2 ) INFORMATION FOR SEQ ID NO:39:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

```
Trp Thr Lys Lys Pro Asn Arg Asn Ala Gly Gly
1               5                   10
```

( 2 ) INFORMATION FOR SEQ ID NO:40:

( i ) SEQUENCE CHARACTERISTICS:
 ( A ) LENGTH: 11 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:40:

Trp Thr Lys Lys Pro Asn Arg Asn Gly Ala Gly
1               5                   10

( 2 ) INFORMATION FOR SEQ ID NO:41:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:41:

Trp Thr Lys Lys Pro Asn Arg Asn Gly Gly Ala
1               5                   10

( 2 ) INFORMATION FOR SEQ ID NO:42:

( i ) SEQUENCE CHARACTERISTICS:
  ( A ) LENGTH: 20 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:42:

Tyr Ala Ala Gln Asn Arg Arg Gly Leu Asp Leu Leu Phe Trp Glu Gln
1               5                   10                  15

Gly Gly Leu Cys
            20

( 2 ) INFORMATION FOR SEQ ID NO:43:

( i ) SEQUENCE CHARACTERISTICS:
  ( A ) LENGTH: 27 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:43:

Leu Pro Pro Thr Ala Pro Pro Leu Leu Pro His Ser Asn Leu Asp His
1               5                   10                  15

Ile Leu Glu Pro Ser Ile Pro Trp Lys Ser Lys
            20                  25

( 2 ) INFORMATION FOR SEQ ID NO:44:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:44:

Arg Val Asn Glu Ile Leu His Ile Leu
1               5

(2) INFORMATION FOR SEQ ID NO:45:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:45:

Lys Lys Pro Asn Arg Asn Gly Gly Gly
1               5

(2) INFORMATION FOR SEQ ID NO:46:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:46:

Lys Pro Asn Arg Asn Gly Gly Gly
1             5

SYNTHETIC PEPTIDES

This invention was made with Government support under grant number CA-40660 awarded by the National Institutes of Health. The Government may have certain rights in this invention.

This is a continuation of application Ser. No. 07/771,553, filed Oct. 8, 1991, now abandoned; which is a CIP of application Ser. No. 07/741,226 filed Aug. 5, 1991, now abandoned; which is a continuation of application Ser. No. 07/303,436 filed Jan. 30, 1989, now abandoned; which is a CIP of Ser. No. 07/153,420, filed Feb. 8, 1988, now abandoned.

BACKGROUND OF THE INVENTION

TECHNICAL FIELD

The present invention relates, in general, to immunogenic preparations and, in particular, to synthetic peptides having amino acid sequences corresponding to antigenic determinants of the envelope proteins of human T-cell leukemia virus (HTLV) types I or II, and immunogenic compositions comprising same.

BACKGROUND INFORMATION

HTLV-I and -II are exogenous, naturally occurring human retroviruses that preferentially infect thymus-derived (T) lymphocytes. HTLV-I and -II are causative agents of adult T-cell leukemias and lymphomas (ATLL) (Poiesz et al. *Proc. Natl. Acad. Sci. USA* 77:7415, 1980; Kalyanaraman et al. Science 218:571, 1982). HTLV-I infection in man can be associated with a "smoldering" pre-leukemic condition that can progress to an overt aggressive ATLL or can remain unchanged for years (Yamaguchi et al. Blood 62:758, 1983). The apparent long latency period prior to onset of ATLL presents a major epidemiological problem in containing the spread of infection by healthy, HTLV-I+ carriers and in identifying those exposed to the virus. HTLV-I can be transmitted by sexual intercourse, shared intravenous drug-abuse equipment, breast milk, and in utero or peripartum exposure (Wong-Staal and Gallo *Nature* 317:395, 1985). Currently, there is no way to eliminate HTLV-I from infected humans or to prevent viral transmission or development of disease.

In addition to ATLL, HTLV-I infection has also been associated with tropical spastic paraparesis (Gessain et al. *Lancet* II:698, 1986), chronic progressive myelopathies (Osame et al. *Ann. Neurol.* 21:117, 1987), multiple sclerosis (Koprowski et al. Nature 318:154, 1985), non-Hodgkin's lymphomas (Gibbs et al. *Assoc. Intern. Med.* 106:361, 1987), and B-cell chronic lymphocytic leukemia (CLL) (Mann et al. Science 236;1103, 1987). HTLV-II has been associated with a rare form of chronic leukemia called T-cell variant of Hairy Cell Leukemia (Kalyanaraman et al. Science 218:571, 1982).

While HTLV-I has a world-wide distribution, localized endemic regions have been identified in southern Japan (Hiruma et al. *Int. J. Cancer* 29:631, 1983), the Caribbean basin (Blattner et al. Lancet II:61, 1983), southeastern United States (Blayney et al. *J. Am. Med. Assoc.* 250:1048, 1983), Africa (Biggar et al. *Int. J. Cancer* 34:215, 1984), and other regions. The epidemiology of HTLV-II is less well known, although the prevalence of HTLV-II seropositivity is increasing (Rosenblatt et al. *New Engl. J. Med.* 315:372, 1986). Similarly, rates of seropositivity for HTLV-I are increasing in intravenous drug abusers from New York City (9%, (Robert-Guroff et al. *J. Am. Med. Assoc.* 255:3133, 1986)) and New Orleans (49% (Weiss et al. *Proc. Am. Soc. Clin. Onc.* 6:5, 1987)) and in subjects receiving transfusions of blood products from New York City (9% (Robert-Guroff et al. *J. Am. Med. Assoc.* 255:3133, 1986)) and Chapel Hill, North Carolina (13%, (Haynes etal. *Clin, Res.* 33:342A, 1985)).

Recently, a cluster of 6 individuals from Raleigh, N.C. was identified with antibodies to HTLV-I (Weinberg et al. *Centers for Disease Control, Morbidity and Mortality Weekly Report*, Dec. 18, 1987). These individuals also had abnormal circulating lymphocytes, indicative of a pre-leukemic syndrome. One patient has subsequently died of adult T-cell leukemia, all 6 were seronegative for HIV. The finding of this cluster, as well as increasing rates of seropositivity in New York City and New Orleans, underscore an immediate need for both reliable diagnostic assays for HTLV-I and for a protective vaccine for non-infected individuals.

Currently, there are no vaccines available for HTLV-I, although results of a number of studies indicate that a vaccine incorporating envelope gene products of HTLV-I is likely to have protective value. The envelope gene of HTLV-I encodes a 63–67 kilodalton (kd) glycoprotein precursor that is proteolytically processed to give rise to a mature gp46 external envelope glycoprotein and a 21kd transmembrane protein (Lee et al. *Proc. Natl. Acad. Sci. USA* 81:3856, 1984).

Kiyokawa et al (*Proc. Natl. Acad. Sci. USA* 81:6202, 1984) have expressed in *E. coli* the entire gp63 envelope precursor molecule of HTLV-I as two fragments, an N-terminal portion containing all but 12 amino acids of the external gp46 envelope molecule and a C-terminal portion consisting almost entirely of the gp21 transmembrane molecule. Using rabbit antisera to the N- and C-terminal portions of HTLV-I gp63 envelope precursor, Kiyokawa et al have neutralized both American and Japanese HTLV-I pseudotypes. Hoshino et al (*Int. J. Cancer* 36:761, 1985) have confirmed this finding with anti-gp21 antiserum. Collectively, these data indicate the presence of at least 2 neutralizing sites on HTLV-I envelope, one associated with the external gp46 envelope glycoprotein and a second associated with the gp21 transmembrane glycoprotein. Moreover, since these HTLV-I recombinant proteins produced in *E. coli* are not glycosylated, carbohydrate is not an essential component of these neutralizing sites.

Thus, synthetic peptides, as non-glycosylated constructs, are likely to be suitable for raising neutralizing antisera to HTLV-I envelope. Since human or animal antisera to Japanese and American HTLV-I envelope will cross-neutralize in pseudotype assays, it is also likely that the envelope antigens of HTLV-I represent a single serotype world-wide (Nagy et al. *Int. J. Cancer* 32:321, 1983). Thus, unlike the isolate-specific neutralizing epitopes of HIV, a synthetic vaccine against one HTLV-I isolate should protect against other HTLV-I isolates. In fact, Tochikuro et al. (*Int. J. Cancer* 36:1, 1985) have demonstrated that HTLV-I specific antibodies can suppress vital antigen expression when added to cultures of HTLV-I+ lymphocytes, suggesting a mechanism whereby anti-HTLV-I antibodies might protect in vivo.

While these data provide strong support for the proposal that portions of HTLV-I envelope glyco- proteins can be used as a vaccine to elicit protective antibody titers to HTLV-I in humans, these studies do not identify the sequence of the critical epitope(s). Elucidation of the sequence(s) should also facilitate identification of the epitope(s) of HTLV-II envelope glycoproteins that would be important for inclusion in a vaccine for HTLV-II, due to the sequence homology that exists between HTLV-I and HTLV-II envelope glycoproteins.

OBJECTS OF THE INVENTION

It is an object of the present invention to provide synthetic peptides that either alone, or when linked to a carrier molecule, and/or polymerized to form molecular aggregates, are capable of inducing in mammals the production of high titers of neutralizing antibodies against HTLV-I or HTLV-II.

It is another object of the invention to provide an immunogenic conjugate comprising a peptide having an amino acid sequence corresponding to an antigenic determinant of the HTLV-I envelope protein that is capable of inducing protective immunity in a mammal against HTLV-I.

It is a further object of the invention to provide an immunogenic conjugate comprising a peptide having an amino acid sequence corresponding to an antigenic determinant of the HTLV-II envelope protein that is capable of inducing protective immunity in a mammal against HTLV-II.

It is an additional object of the invention to provide a method of detecting the presence of anti-HTLV-I or anti-HTLV-II antibodies in a biological test sample.

These, and other objects that will be clear to those skilled in the art from the following detailed description, have been accomplished by providing synthetic peptides useful in producing an immunogenic response to the viral causative agents of HTLV-I and HTLV-II.

SUMMARY OF THE INVENTION

The invention relates to immunogenic preparations and vaccines made therefrom. Synthetic peptides having amino acid sequences corresponding to antigenic determinants of the envelope proteins of either HTLV-I or HTLV-II are covalently coupled, either directly or through spacer molecules, to suitable carrier molecules to form immunogenic conjugates. Vaccines comprising one or more such conjugates are disclosed.

In one embodiment, the present invention comprises a synthetic peptide having an amino acid sequence corresponding to an antigenic determinant of the envelope glycoprotein of HTLV-I (or HTLV-II), which peptide is capable, either alone or when covalently linked to a carrier molecule, of inducing in a mammal high titers of protective antibodies against HTLV-I (or HTLV-II). The peptide of the instant invention corresponds to an antigenic determinant present in a hydrophilic region (Kyte and Doolittle *J. Mol. Biol.* 157:105, 1982) of an HTLV-I (Seiki et al. *Proc. Natl. Acad Sci. USA* 80:3618, 1983) or HTLV-II (Sodroski et al. *Science* 225:421, 1984)) envelope glycoprotein.

In another embodiment, the present invention comprises an immunogenic conjugate capable of inducing in a mammal high titers of protective antibodies against HTLV-I (or HTLV-II), said conjugate comprising: (i) a carrier molecule covalently attached to (ii) a synthetic peptide having an amino acid sequence corresponding to an antigenic determinant of the envelope glycoprotein of HTLV-I (or HTLV-II).

In yet another embodiment, the present invention comprises a method of producing immunity to HTLV-I (or HTLV-II) comprising administering the above-described HTLV-I (or HTLV-II) specific conjugate to a mammal in an immunogenically effective amount.

In another embodiment, the present invention comprises a method of detecting the presence of anti-HTLV-I (or anti-HTLV-II) antibodies in a biological test sample comprising contacting a peptide of the instant invention with the sample, allowing antibodies in the sample to complex with the peptide, and measuring the formation of the complex.

BRIEF DESCRIPTION OF THE DRAWINGS

FIG. 6: Peptide absorption of neutralizing antibodies to HTLV-I.

DETAILED DESCRIPTION OF INVENTION

Figure 1:
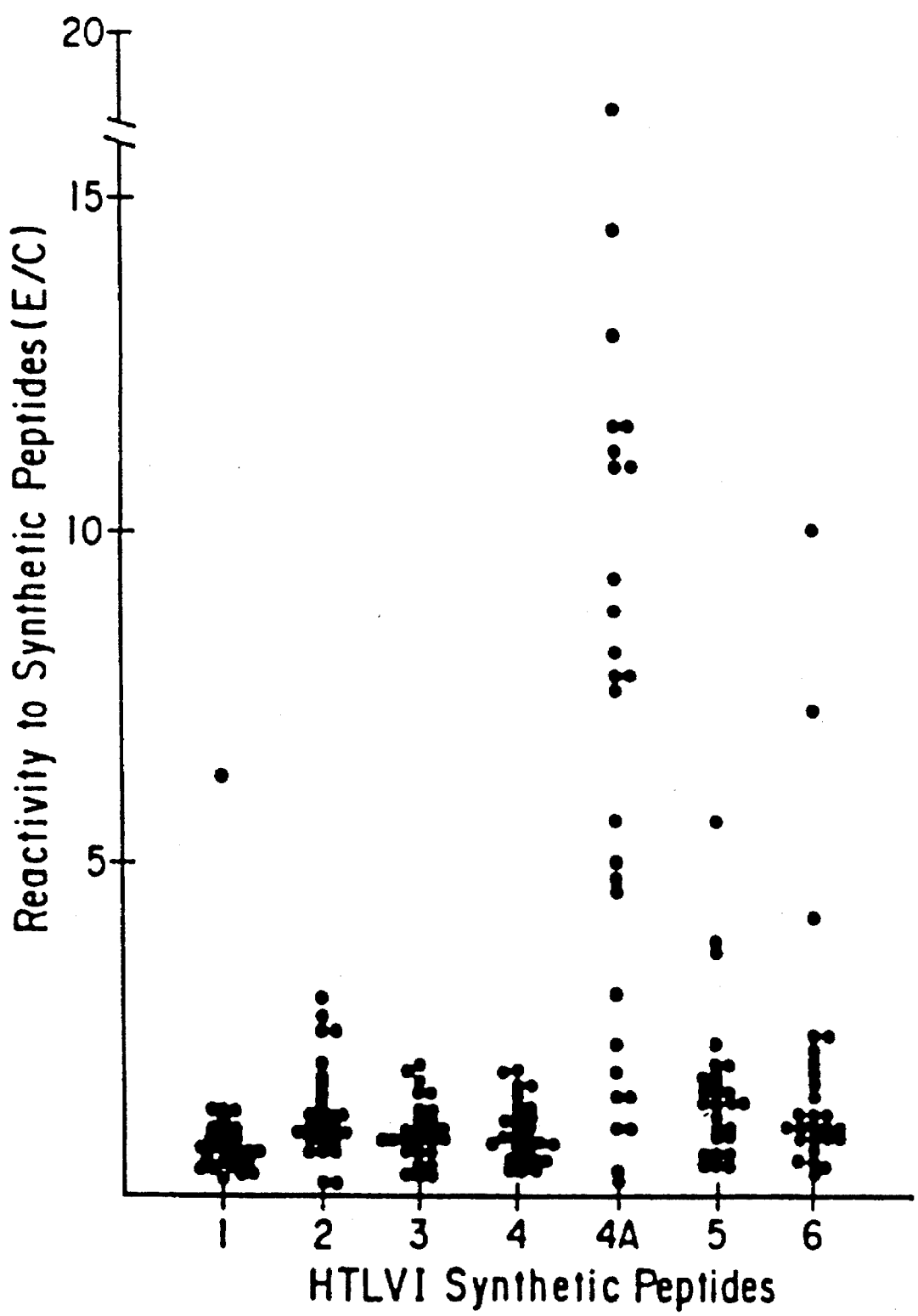
FIG. 1.: Reactivity of antibodies from HTLV-I+ patients to gp46 env-encoded synthetic peptides.

The present invention relates to peptides corresponding to immunogenic epitopes of HTLV-I and to peptides corresponding to immunogenic epitopes of HTLV-II, and to synthetic vaccines against HTLV-I and HTLV-II, respectively, made therefrom. These novel immunogenic agents are prepared by chemically synthesizing peptides sharing antigenic determinants with the gp46 envelope protein of HTLV-I or HTLV-II. The peptides are linked to carrier molecules, thus, forming immunogenic conjugates (and/or are polymerized), rendering them suitable as vaccines. These vaccines are useful for immunization against HTLV-I- or HTLV-II-related diseases when administered in an immunogenically effective amount to a mammal, for example, by the parenteral route.

It was determined that peptides that should be studied for immunogenic potential included those corresponding to hydrophilic, charged regions of the HTLV-I and HTLV-II gp46 envelope glycoproteins. It was further determined that, of such peptides, those with predicted beta turns would likely be of particular importance. It was recognized that the formation of intrapeptide disulfide bonds would be useful in establishing native configurational determinants. Also, it was recognized that formation of interchain disulfide bonds would be useful in polymerizing peptide molecules so as to form larger, more immunogenic peptide aggregates.

Computer analysis of the predicted amino acid sequences of the envelope proteins of HTLV-I and HTLV-II established the secondary structure and location of hydrophilic regions. Secondary structure was determined from the computer analysis using the method of Chou and Fasman (*Biochemistry* 131211 and 131222, 1974; *Advances in Enzymology* 47145, 1978). Potential areas of beta turns were localized using the method of Rose (Nature 272:586, 1978). Hydrophilic regions of the envelope protein were identified by the technique of Rose and Roy *(Proc. Natl. Acad. Sci. USA*

7714643, 1980) and Kyte and Doolittle (*J. Mol. Biol.* 157:105–132, 1982).

The peptides of the instant invention include peptides that correspond to, or are homologous with, B-cell epitopes present within the gp46 envelope glycoprotein of HTLV-I. These peptides are about 25 amino acids (units) or less in length, are hydrophilic, and when conjugated to an appropriate carrier molecule, evoke the production in a mammal of high titers (1:1000) of anti-peptide antibodies that can react with the native gp46 envelope glycoprotein of HTLV-I. Other peptides of the instant invention correspond to, or are homologous with, B-cell epitopes present within the gp46 envelope glycoprotein of HTLV-II. These peptides are also about 25 amino acids (units) or less in length, are hydrophilic, and when conjugated to an appropriate carrier molecule, should evoke the production in a mammal of high titers (1:1000) of anti-peptide antibodies that can react with the native gp46 envelope glycoprotein of HTLV-II.

The synthetic peptides of the present invention can have an amino acid sequence as shown in Table 1, or a sequence which is similar enough to one of the sequences shown in Table 1 so as to be treated in the same manner by an antibody which bonds with the epitope represented by the specific sequence given in the table (that is, an immunogenically comparable sequence). An example of such a similar sequence is WTKKPNRNGGG (SEQ ID NO: 1)(amino acid numbers 88–98 of HTLV-I envelope; designated SP 2L-1). Such synthetic peptides are hereinafter designated "HTLV-I-specific peptides".

Table 2 so as to be treated in the same manner by an antibody which bonds with the epitope represented by the specific sequence given in the table (that is, an immunogenically comparable sequence). An example of such a similar sequence is PHWIKKPNRQGLGYYS(C)(SEQ ID NO:14) (amino acid numbers 82–97 of HTLV-II envelope; designated DP-90). Such synthetic peptides are hereinafter designated "HTLV-II-specific peptides".

TABLE 1

Synthetic Peptides for Use in Diagnosis and Vaccination Against HTLV-I

| Peptide # | Envelope[1] Amino Acid # | Amino Acid Sequence[2,3,4] |
|---|---|---|
| 1 | 33–47 | VSSYHSKPCNPAQPV (SEQ ID NO: 2) |
| 2 | 86–107 | (C)PHWTKKPNRNGGGYYSASYSDP (SEQ ID NO: 3) |
| 3 | 176–189 | (C)LNTEPSQLPPTAPP(Y) (SEQ ID NO: 4) |
| 4 | 129–149 | SSPYWKFQHDVNFTQEVSRLN(C) (SEQ ID NO: 5) |
| 4A | 190–209 | (C)LLPHSNLDHILEPSIPWKSK(Y) (SEQ ID NO: 6) |
| 5 | 269–280 | (Y)LPFNWTHCFDPQ(C) (SEQ ID NO: 7) |
| 6 | 296–312 | (C)PPFSLSPVPTLGSRSRR (SEQ ID NO: 8) |
| 7 | 374–392 | YAAQNRRGLDLLFWEQGGL(C) (SEQ ID NO: 9) |
| 8 | 400–415 | CRFPNITNSHVPILQE (SEQ ID NO: 10) |
| 9 | 411–422 | (C)PILQERPPLENR (SEQ ID NO: 11) |
| 10 | 462–480 | CILRQLRHLPSRVRYPHYS (SEQ ID NO: 12) |
| 11 | 475–488 | (C)RYPHYSLIKPESSL (SEQ ID NO: 13) |

[1]According to Seiki, M. et al. Proc. Natl. Acad. Sci. USA 80:3618–3622, 1983; N-terminal methionine of leader sequence = 1.
[2]Sequences of synthetic peptides 1–11 are listed sequentially from N— to C— terminus of the HTLV-I gp63 envelope precursor molecule with the exception of peptide 4. Sequences in peptides 1–6 are from gp46 external envelope glycoprotein while sequences in peptide 7–11 are derived from gp21 transmembrane glycoprotein. Amino acid numbers begin with the initiation methionine = 1. (See Palker et al J. Immunol (1989) Vol. 142 (Feb. 1).)
[3]Amino acids in parentheses were added to facilitate coupling to carrier protein (C) and iodination (Y) of peptide. Cys can be either at N— or C— terminus.
[4]Each amino acid is represented by its single - letter code, which is the first letter of its name, except for arginine (R), aspartic acid (D), asparagine (N), glutamine (Q), glutamic acid (E), lysine (K), phenylalanine (F), tryptophan (W), and tyrosine (Y).

Similarly, other synthetic peptides of the instant invention can have an amino acid sequence as shown in Table 2, or a sequence similar enough to one of the sequence shown in

TABLE 2

| | | Synthetic Peptides for Use in Diagnosis and Vaccination Against HTLV-II |
|---|---|---|
| Peptide # | Envelope[1] Amino Acid # | Amino Acid Sequence[2,3] |
| 1 | 30–44 | SSYHSSPCSPTQPVC (SEQ ID NO: 15) |
| 2 | 44–63 | CTWNLDLNSLTTDQRLHPPC (SEQ ID NO: 16) |
| 3 | 83–104 | HWIKKPNRQGLGYYSPSYNDPC (SEQ ID NO: 17) |
| 4 | 125–140 | (C)SSPSWKFHSDVNFTQE (SEQ ID NO: 18) |
| 5 | 174–194 | (C)SEPTQPPPTSPPLVHDSDLEH (SEQ ID NO: 19) |
| 6 | 295–308 | (C)SLAPVPPPATRRRR (SEQ ID NO: 20) |

[1]According to Sodroski et al. Science 225:421–424, 1984. Methionine of leader sequence = 1.
[2]Amino acids in parentheses were added to facilitate coupling to carrier protein (C) and iodination (Y) of peptide. Cys can be either at N— or C— terminus.
[3]Each amino acid is represented by its single - letter code, which is the first letter of its name, except for arginine (R), aspartic acid (D), asparagine (N), glutamine (Q), glutamic acid (E), lysine (K), phenylalanine (F), tryptophan (W), and tyrosine (Y).

Carrier molecules to which peptides of the invention are covalently linked (conjugated) are advantageously non-toxic, pharmaceutically acceptable, and of a size sufficient to produce an immune response in a mammal. Examples of suitable carrier molecules include tetanus toxoid, and key-hole limpet hemocyanin (KLH). Other carrier molecules to which HTLV-I-specific and HTLV-II-specific peptides can be linked include peptides comprising sequences corresponding to T-cell epitopes of the HTLV-I or HTLV-II gp63 envelope glycoprotein or p55 gag polyprotein having helical structures predicted by the algorithm of Margalit et al. (*J. Immunol.* 38:2213, 1987), specific examples of which are given in Table 3. The addition of LASGKSL amino acids to the N-terminus of I-T1 result in a peptide identified by murine T-helper cells.)

TABLE 3

| | | T Cell Epitopes of HTLV-I and HTLV-II1 | | |
|---|---|---|---|---|
| VIRUS | GENE | AMINO ACID # | DESIGNATION | SEQUENCE[2,3] |
| HTLV-I | Envelope | 347–363 | I-T1 | LHEVDKDISOLTQAIVK (SEQ ID NO: 21) |
| HTLV-I | Envelope | 64–74 | I-T2 | QPPCPNLVSYS (SEQ ID NO: 22) |
| | Gag | 184–200 | I-T3 | DLQDLLQYLCSSLVASL (SEQ ID NO: 23) |
| | Gag | 79–87 | I-T4 | RVNEILHIL (SEQ ID NO: 24) |
| HTLV-II | Envelope | 348–369 | II-T4 | KDISHLTQAIVKNHQN- (SEQ ID NO: 25) ILRVAQ (SEQ ID NO: 26) |

[1]Algorithm of Margalit et al. J. Immunol. 138:2213, 1987 use to predict amino acid sequences containing amphipathic a helical secondary structures.
[2]HTLV-I predicted amino acid sequence from Seiki et al. Proc Natl. Acad. Sci. USA 80:3618, 1983.
[3]HTLV-II predicted amino acid sequence from Sodroski et al. Science 225:421, 1984.

HTLV-I- and HTLV-II-specific peptides can also be administered with a pharmaceutically acceptable adjuvant, for example, alum, or conjugated to other carrier molecules more immunogenic than tetanus toxoid.

Linkage of a carrier molecule to HTLV-I- or HTLV-II-specific peptides of the invention can be direct or through a spacer molecule. Spacer molecules are, advantageously, non-toxic and reactive. Two glycine residues added to the amino terminal end of an HTLV-I- or HTLV-II-specific peptide can provide a suitable spacer molecule for linking the peptide to a carrier molecule; alternatively, HTLV-I- or HTLV-II-specific peptides can, for example, be synthesized directly adjacent to, for example, another immunogenic HTLV-I or HTLV-II envelope sequence, for example, such as those sequences (or portions thereof) shown in Table 3. Cysteines can be added either at the N- or C-terminus of the HTLV-I- or HTLV-II-specific peptides for conjugation to the carrier molecule, or to both ends to facilitate interchain polymerization via disulfide bond formation to form larger molecular aggregates.

Conjugation of the carrier molecule to the HTLV-I- or HTLV-II-specific peptide is accomplished using a coupling agent. Advantageously, the heterofunctional coupling agent M-maleimidobenzoyl-N-hydroxysuccinimide ester (MBS), or the water soluble compound m-maleimido-benzoylsulfo-succinimide ester (sulfo-MBS), is used, as described by Green et al. (*Cell* 28:477, 1982) and by Palker et al. (*Proc. Natl. Acad. Sci. USA* 84:2479, 1987).

Vaccines of the instant invention, which, when administered to a mammal, induce a protective immunogenic response against HTLV-I, comprise one or more immunogenic conjugate(s), each conjugate comprising an HTLV-I-specific peptide, wherein each HTLV-I-specific peptide corresponds to a different portion of the HTLV-I gp46 envelope protein. Advantageously, one or more of the HTLV-I-specific peptides listed in Table 1 is conjugated to, or synthesized with, a predicted T-cell epitope of HTLV-I envelope or gag proteins, for example, those shown in Table 3. An example of such a "chimera" is LPPTAPPLLPHSNLDHI-LEPSIPWKSKWTKKPNRNGGG (SEQ ID NO: 25)(amino acid numbers 183–209/88–98 of HTLV-I envelope; designated DP-91).

Similarly, vaccines of the present invention capable of inducing a protective immunogenic response against HTLV-II, comprise one or more immungenic conjugate(s), each conjugate comprising an HTLV-II-specific peptide, wherein each peptide corresponds to a different portion of the HTLV-II gp46 envelope protein. Advantageously, one or more of the HTLV-II-specific peptides listed in Table 2 is conjugated to, or synthesized with, a predicted T-cell epitope, for example, those shown in Table 3.

In addition, a bivalent vaccine can be constructed whereby immunogenic conjugates as described above, comprising synthetic peptides from envelope proteins of HTLV-I and HTLV-II, are mixed to form a single inoculum such that protective antibodies will be simultaneously raised in a mammal to HTLV-I and HTLV-II.

The advantage of using, as a carrier molecule, a synthetic peptide reflecting a portion of HTLV-I or -II envelope or gag molecules recognized by helper T cells, is that no other carrier molecule, such as tetanus toxoid, is required, and the B and T cell response to HTLV-I, or HTLV-II, is specific. HTLV-I- and HTLV-II-specific peptides, alone or synthesized with a corresponding T cell epitope, can be treated with oxidizing agents to induce disulfide bond formation between peptide chain cysteines, to effect polymerized and therefore, highly immunogenic antigens.

The ability of HTLV-I- and HTLV-II-specific peptides of the instant invention to produce neutralizing antibodies following immunization is determined as described by Nagy et al (*Int. J. Cancer* 32:321, 1983).

In addition to the use of HTLV-I- and HTLV-II-specific peptides as a vaccine, or as a component of a vaccine, these peptides can also be used for diagnostic purposes. The presence and titers of antibodies to HTLV-I or HTLV-II envelope proteins in biological samples can be detected using HTLV-I- and HTLV-II-specific peptides in a solid phase radioimmunoassay (RIA) (Palker et al *J. Immunol.* 136:2393, 1986—the entire contents of which document is hereby incorporated by reference; *ibid., Proc. Natl. Acad, Scl. USA* 84:2479, 1987) HTLV-I- and HTLV-II-specific peptides of the instant invention can also be used in standard enzyme-linked immunosorbent assays (ELISA) to detect the presence of antibodies to HTLV-I or HTLV-II envelope glycoproteins in biological samples.

In one embodiment of the HTLV-I diagnostic assay of the present invention, a mixture of synthetic peptides from HTLV-I gp46 envelope and HTLV-I p19 gag proteins are used, advantageously peptide 4A of Table 1 and a peptide containing the following carboxy-terminal sequence of HTLV-I p19: Pro-Tyr-Val-Glu-Pro-Thr-Ala-Pro-Gln-Val-Leu (SEQ ID NO: 26). In combination, these two peptides are recognized by antibodies in 95% of sera from HTLV-I+ subjects having antibodies to p19 or gp46 (Palker et al. *J. Immunol.* 136:2393, 1986, and FIG. 1). A combination of these two peptides can be used in an ELISA or a RIA to detect antibodies in sera from HTLV-I+ patients.

In view of the foregoing, it will be clear to those of ordinary skill in the art that HTLV-I and HTLV-II specific test kits can be constructed for detecting antibodies to HTLV-I and HTLV-II in biological samples using techniques for detection that include ELISA, RIA, indirect immunofluorescence and Western blot analysis.

It will also be clear to those of ordinary skill in the art that antibodies produced in response to immunization with the HTLV-I- or HTLV-II-specific peptides of the instant invention can be used in an antigert diagnostic assay using standard techniques.

The following nonlimiting Examples illustrate the invention in more detail:

EXAMPLE 1

Synthesis of HTLV-I- and HTLV-II-Specific Peptides and Preparation of Conjugates Synthetic essentially pure peptides containing hydrophilic amino acid sequences from HTLV-I gp46 (Seiki et al. *Proc. Natl. Acad. Sci. USA* 80:3618–3622, 1983) and HTLV-II gp46 (Sodroski et al. Science 225:421–424, 1984) were synthesized on a Dupont 2100 peptide synthesizer using chemicals and program cycles supplied by the manufacturer. Sequences are given in Tables 1 and 2.

Peptides were conjugated to the carrier molecule tetanus toxoid (TT) with MBS, as described by Green et al. (*Cell* 28:477, 1982; Palker et al. *Proc. Natl, Acad. Sci. USA* 84:2479, 1987). For the coupling procedure, 24 mg of tetanus toxoid in 0.5 ml of phosphate buffered saline, pH 7.2, was incubated with 1 mg of MBS dissolved in 100 μl of dimethylformamide for 1 hr. at 23° C. Tetanus toxoid treated with MBS (TT-MBS) was then subjected to sieving chromatography on a PD-10 (Pharmacia) column to remove unreacted MBS from TT-MBS, and fractions containing TT-MBS were recovered in the void volume of the column as determined by spectrophotometric assay at an optical density of 280 nm. TT-MBS was then incubated with rocking at 23° C. for 3 hr. with 6–9 mg of synthetic peptide (molar ratio 30:1, peptide carrier protein) in PBS containing reduced cysteine at either the carboxyl or amino terminus. TT-peptide conjugates were dialyzed overnight at 4° C. against PBS or again desalted on a PD-10 column and were used as an immunogen.

Conjugation of peptides to carrier molecule toxoid was monitored by subjecting conjugates to sodium dodecylsulfate-polyacrylamide gel electrophoresis (SDS-PAGE) and by measuring the increase in apparent molecular weights over that of carrier molecule polyacrylamide gel electrophoresis (SDS-PAGE) and by measuring the increase in apparent molecular weights over that of carrier molecule treated with MBS. Coupling efficiencies, also monitored by trace iodination of peptides, varied from 10–30% depending on the peptide.

EXAMPLE 2

Reactivity of Antibodies from HTLV-I Seropositive subjects to HTLV-I gp46 Synthetic Peptides.

Synthetic peptides derived from hydrophilic regions of HTLV-I gp46 (HTLV-I-synthetic peptides) were dissolved or suspended in 0.1M NaHCO buffer, pH 9.6 and 50 μg/well were incubated in Immulon 2 microtiter wells (Dynatech) overnight at 4° C. Wells were emptied, and 200 μof 5% nonfat dry milk (Carnation) in phosphate buffered saline (PBS) and 0.1% sodium azide were added to wells and incubated for 2 hr. Wells were emptied, washed once with PBS containing 5% nonfat dry milk and 0.05% Tween 20 (wash buffer) and incubated further with 1:50 dilutions of sera from either HTLV-I+ patients or normal subjects in wash buffer for 1 hr. Wells were washed X3 in wash buffer, further incubated with a 1:150 dilution of rabbit anti-human IgG (H & L chain specific, Cooper Biomedical, Malvern, Pa.) whole serum in wash buffer (50 μl) for 30 min, washed as before and further incubated with $10^5$ cpm of 125I-labeled protein A (Sigma) in 50 μl wash buffer for 30 min at 23° C. Wells were washed as before, and radioactivity bound to wells was measured in a gamma counter. As shown in FIG. (E/C) of mean cpm values (duplicate wells) obtained with experimental (E) HTLV-I+ patient sera and normal serum controls (C). Ratios greater than 2.0 were considered positive.

EXAMPLE 3

Detection of Antibodies to HTLV-I and HTLV-II

HTLV-I encoded synthetic peptides SP-71 (Pro-Tyr-Val-Glu-Pro-Thr-Ala-Pro-Gln-Val-Leu) from the C-terminus of p19 or portions thereof and synthetic peptide SP-4A of Table 1 from gp46 can be mixed, added to microtiter wells (10–50 μg of each peptide per microtiter well) in the RIA described above and used to detect antibodies to HTLV-I. Also, the peptide Pro-Tyr-Val-Glu-Pro-Thr-Thr-Thr-Gln-Cys-Phe (SEQ ID NO: 27) or portions thereof containing an amino acid sequence from the C-terminus of HTLV-II p19 can be added to microtiter wells (10–50 μg/well) as described above and used to detect antibodies to HTLV-II.

EXAMPLE 4

Reactivity of Anti-Synthetic Peptide Antisera to Synthetic Peptides and HTLV-I Envelope Glycoproteins.

HTLV-I env-encoded synthetic peptides (HTLV-I-specific peptides) were covalently linked to tetanus toxoid (TT) as previously described, and used to immunize rabbits. After 1 immunization with 5 mg of peptide-TT conjugate in Freunds complete adjuvant followed by 2 additional weekly boosts with conjugate in Freunds incomplete adjuvant, sera were collected and tested for reactivity to the immunizing peptide (Table 4).

TABLE 4

Rabbit Sera Reactivity to HTLV-I Synthetic Peptides (SP) 1–6

| Antibody | Antigen | | | | | | |
|---|---|---|---|---|---|---|---|
| | SP-1 | SP-2 | SP-3 | SP-4 | SP-4A | SP-5 | SP-6 |
| α SP-1 | 58.1 | 0.5 | 2.1 | 0.4 | 0.9 | 1.3 | 0.4 |
| α SP-2 | 1.3 | 40.3 | 6.6 | 2.3 | 0.8 | 5.0 | 1.1 |
| α SP-3 | 2.0 | 0.4 | 45.6 | 2.0 | 0.9 | 0.9 | 0.9 |
| α SP-4 | 0.4 | 0.5 | 0.7 | 20.9 | 0.6 | 0.4 | 1.1 |
| α SP-4A | 0.7 | 0.9 | 1.0 | 3.0 | 229.5 | 12.1 | 2.8 |
| α SP-5 | 0.5 | 1.6 | 0.9 | 3.2 | 2.5 | 285.4 | 2.0 |
| α SP-6 | 1.5 | 0.8 | 2.4 | 0.7 | 1.4 | 2.5 | 105.5 |

Reactivity of anti-peptide antisera to synthetic peptides was determined in radioimmunoassay (duplicate wells) and results were expressed as a ratio of mean cpm values obtained with immune and pre-immune sera. Anti-peptide antisera had a high degree of specificity to the immunizing peptide (underlined values).

Figure 2:
FIG. 2.: Reactivity of anti-synthetic peptide antisera to gp46 and gp63 envelope glycoproteins of HTLV-I in an immunoblot assay.
Figure 3:
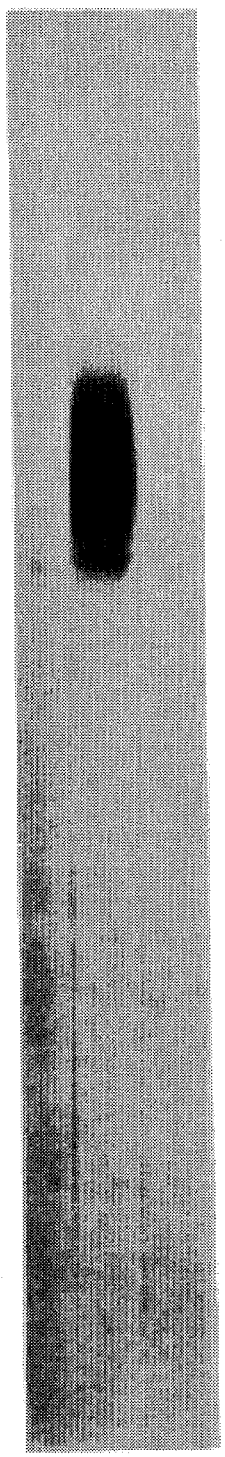
FIG. 3.: Specific inhibition of anti-peptide antibody reactivity to HTLV-I gp46 in an immunoblot assay.

Antisera to HTLV-I synthetic peptides 1–6 reacted with a high degree of specificity to the immunizing peptide with minimum titers of 1:2000 in RIA. When tested in immunoblot assay, antisera to peptides 1, 3, 4, 4A and 6 reacted with HTLV-I gp46 and/or gp63 (lanes 2, 4, 6, 8, 10, respectively), while pre-immune sera (lanes 1, 3, 5, 8, 9) did not react; anti-HTLV-I envelope monoclonal antibody 1C11, used as a positive control, also reacted with gp46 and gp63 (line 12).whereas negative control ascites fluid (P3X63) did not react (lane 11). (FIG. 2). The reactivity of anti-peptide antiserum to gp46 in immunoblot assay could be specifically inhibited by pre-incubating antiserum with the corresponding peptide (FIG. 3). To evaluate the specificity of anti-peptide antibody binding to gp46, antiserum to HTLV-I gp46 peptide SP-6 was pre-incubated with 200 μg of either SP-6 (lane 1) or SP-5 (lane 2) and then reacted with gp46 in immunoblot assay. Synthetic peptide SP-6 completely inhibited anti-SP-6 antibody binding to gp46 (lane 1), while SP-5 did not (lane 2). Shown in lane 3 is the lack of reactivity of normal rabbit serum antibodies (plus peptide SP-6) to gp46. The data indicate that peptides from HTLV-I gp46 (HTLV-I-specific peptides) when coupled to carrier molecules can be used to raise antibodies to HTLV-I gp46.

EXAMPLE 5

Mapping of an Epitope of HTLV-I GP46 Recognized by an HLA-DR2Restricted Cytotoxic T Cell Line P-10 from Patient A with HTLV-I Associated Tropical Spastag Paraparesis (TSP).

Figure 4B:
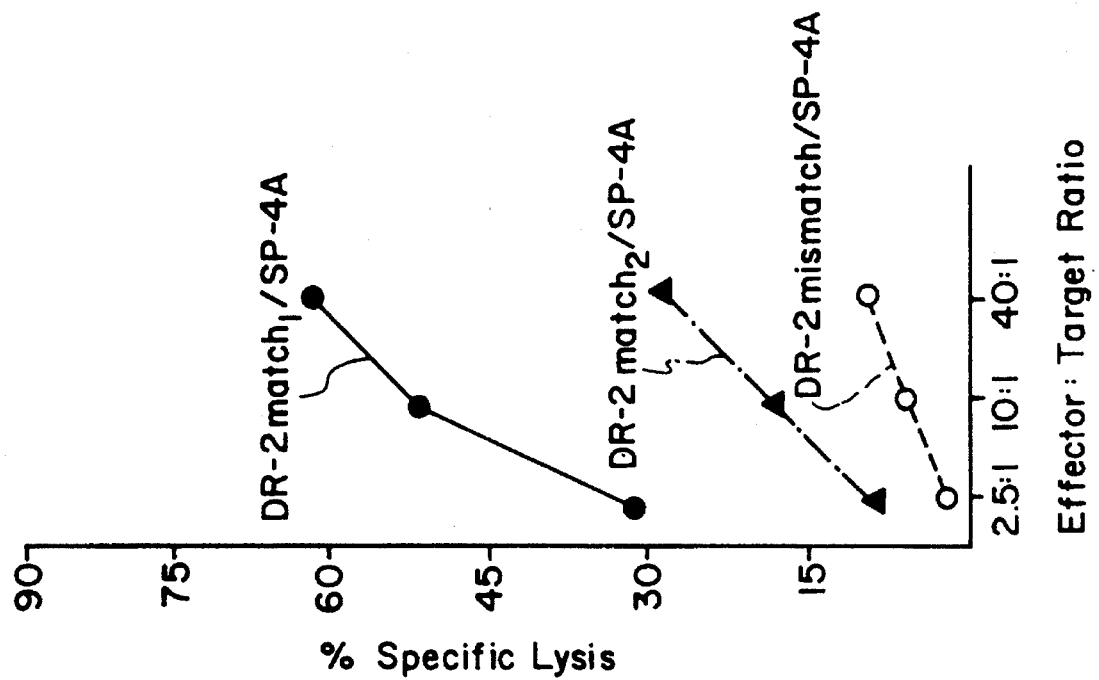
FIG. 4A and 4B: Mapping of an epitope of HTLV-I gp46 that is recognized by an HLD-DR2 restricted cytotoxic T cell line P-10 from patient A with HTLV-I associated tropical spastic paraparesis (TSP).
Figure 4A:
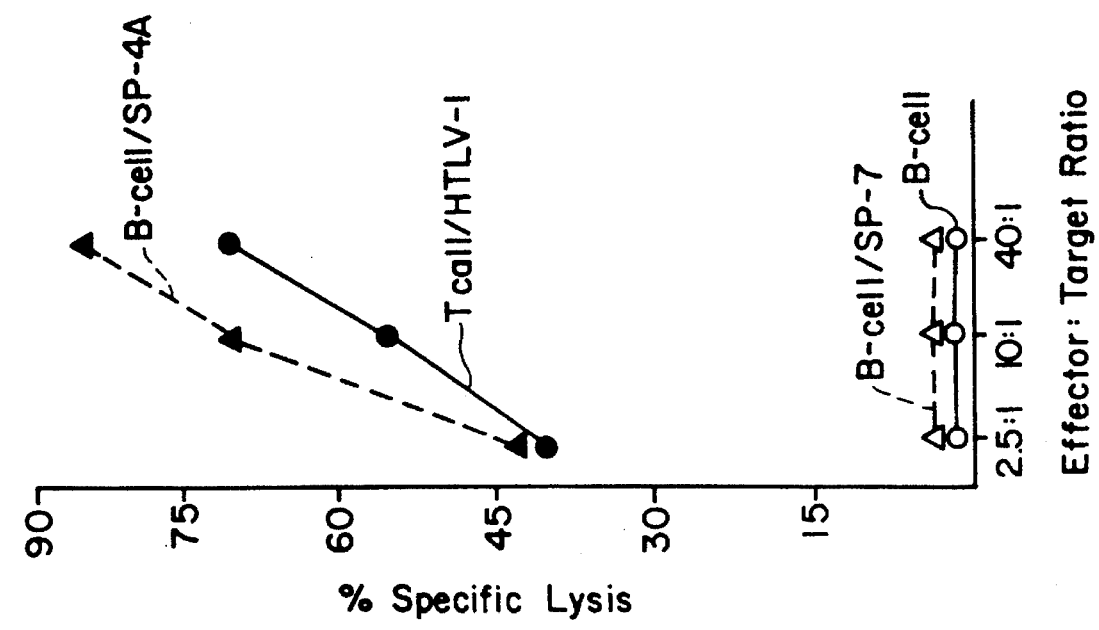

The results shown in FIG. 4A and FIG. 4B were obtained using the method of Jacobson et al. (Viral Immunol. (1987/1988) 1:153–162)

FIG. 4A: EBV-transformed B cells from patient A were incubated with HLTV-I envencoded synthetic peptides 1–11 (Table 1), labelled with $^{51}$Cr and used as targets to assess peptide-specific killing by autologous, cloned, cytotoxic T cell line P-10. B cells coated with peptide SP-4A (Δ—Δ) and autologous T cells infected with HTLV-I (●—●) were both killed by the cytotoxic T cell line P-10 from patient A. Untreated autologous B cells (○—○) or B cells coated with any of the remaining 11 peptides Δ—Δ) were not killed.

Figure 5A:
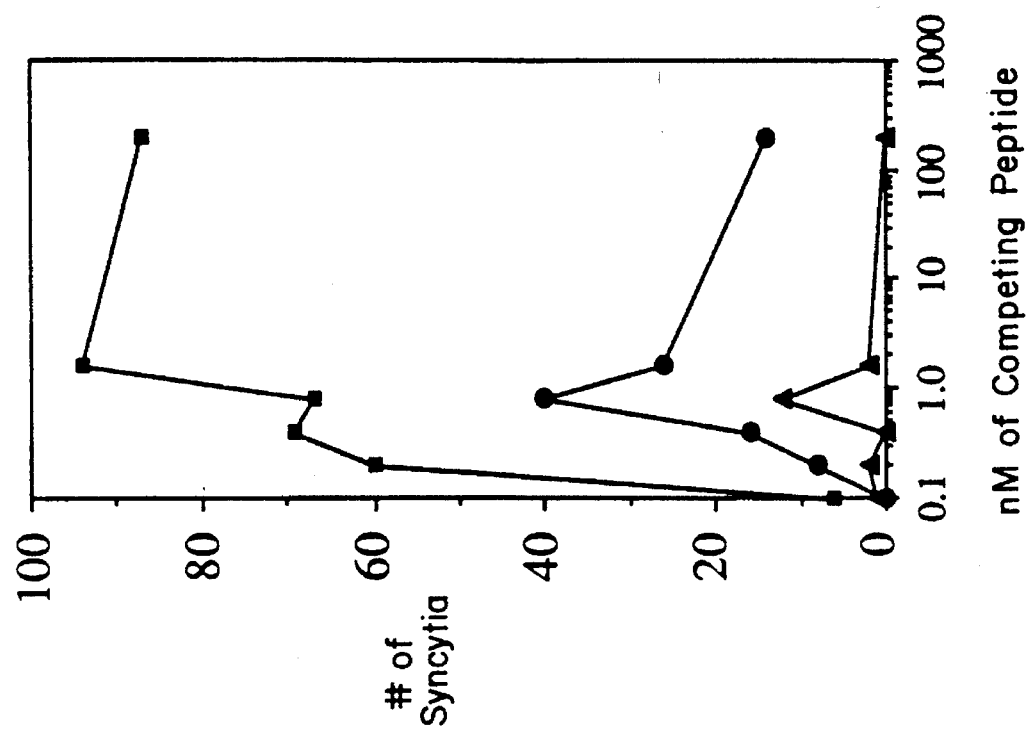
FIG. 5: Absorption of neutralizing anti-peptide antisera with synthetic peptide SP-2.
Figure 5B:
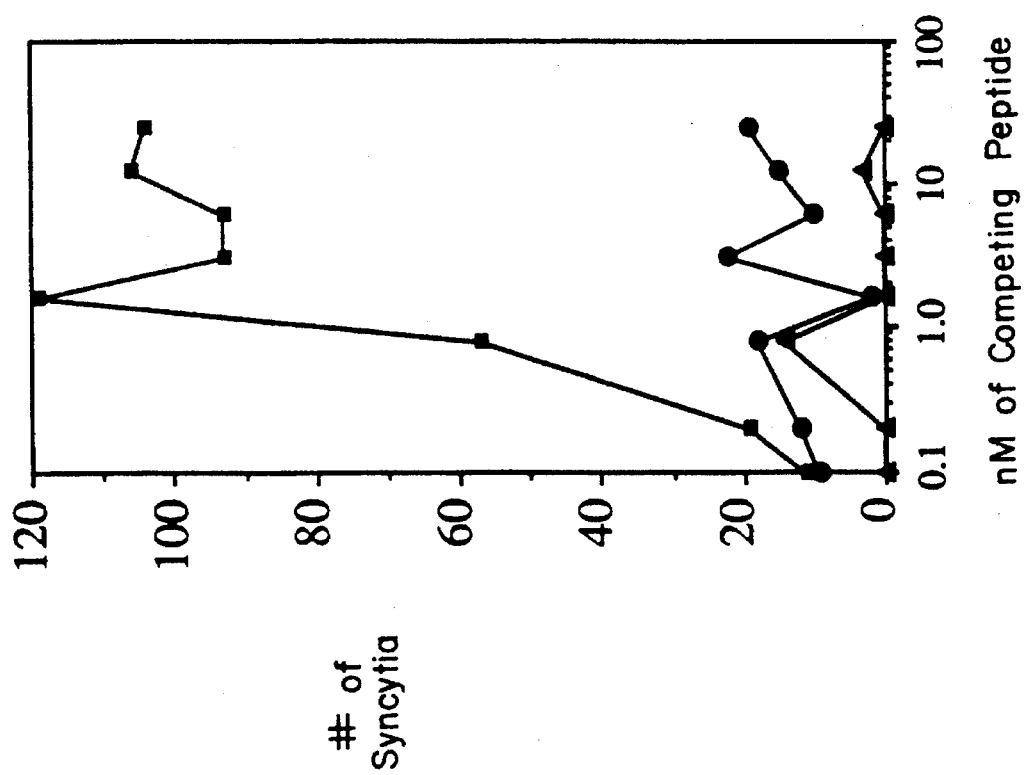
Figure 7:
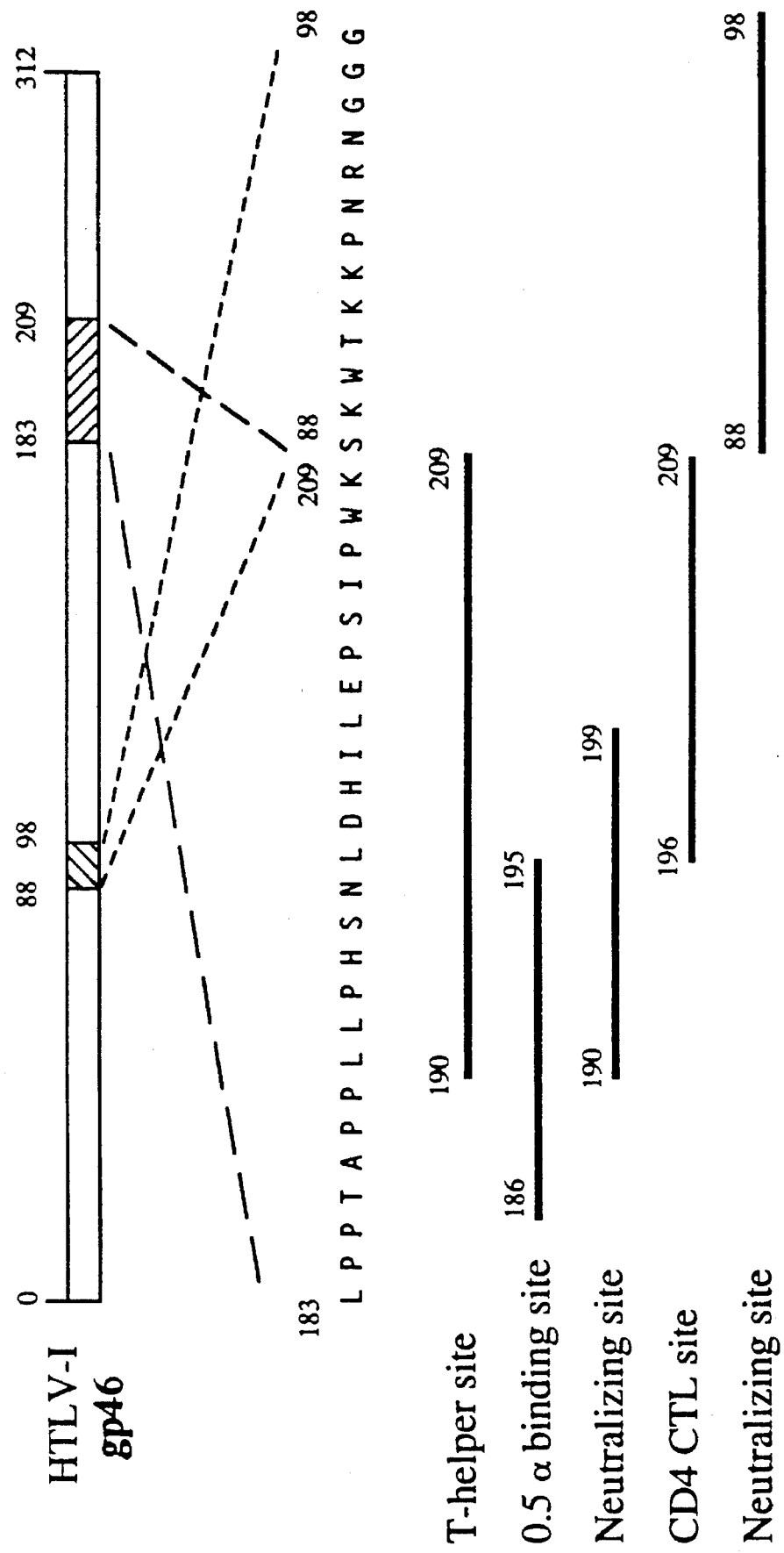
FIG. 7: HTLV-I T-Cell/B-Cell Peptide.

FIG. 5B: Two heterologous B cell lines (●—●, Δ—Δ) matched with the cytotoxic T cell line P-10 at HLA-DR2 and one B cell line mismatched at HLA-DR2 (○—○) were coated with peptide SP-4A and used as targets in cytotoxicity assays as described above. B cells coated with peptide 4A and matched at HLA-DR2 were killed by T cell line P-10 while substantially less killing was observed with HLA-DR2 mismatched B cells coated with SP-4A.

These studies indicate that the region of HTLV-I gp46 defined by peptide SP-4A (amino acids 190–209) contains an epitope identified by an HLA-DR2 restricted cytotoxic T cell line.

EXAMPLE 6

Neutralization of Vesicular Stomatitis Virus (VSV) /Human T-Cell Leukemia virus Type I (HTLV-I) Pseudotype Particles with Antisera to HTLV-I Env-Encoded Synthetic Peptides A. Rabbits were immunized with 5 mg of synthetic peptide—tetanus toxoid conjugates subcutaneously in Freund's complete (day 1) and incomplete (days 8, 15, 22, and 29) adjuvant.

Amino acid sequences of HTLV-I env gene encoded synthetic peptides are given in Table 1.

Data are given as the percent inhibition of VSV (HTLV-I) induced plaque formation. Pseudotype particles containing the VSV genome and HTLV-I envelope glycoproteins were titered to give 150–200 plaques per assay. The assay was performed by Dr. Paul Clapham according to the procedure of Clapham et al. Proc. Natl. Acad. Sci. USA 81:2886, 1984, the entire contents of which document is hereby incorporated by reference.

TABLE 5

| Immunizations per rabbit | Antisera to Peptides | | | | | | | | | | | |
|---|---|---|---|---|---|---|---|---|---|---|---|---|
| | 1 | 2 | 3 | 4 | 4A | 5 | 6 | 7 | 8 | 9 | 10 | 11 |
| Preimmune serum | 0 | 0 | 0 | 0 | 0 | 0 | 0 | 0 | 0 | 0 | 0 | 0 |
| 4 | 50 | 50 | 50 | 0 | 0 | 0 | 0 | ND | ND | ND | ND | ND |
| 5 | 0 | >80 | >80 | 0 | >80 | 0 | 0 | 0 | 0 | 0 | 0 | 0 |

Anti-peptide antisera were raised in two goats (#20, 21) to synthetic peptides SP-2 (containing HTLV-I envelope amino acids 86–107) and SP-3/4A (containing HTLV-I envelope amino acids 176– 209) coupled to tetanus toxoid. Antisera (but not pre-immune sera) from both goats inhibited the ability of HTLV-I infected cells to fuse with uninfected human T-cells (syncytium formation). To determine which peptide was responsible for inducing antibodies in goats 20 and 21 that neutralized HTLV-I, heat-inactivated (56° C., 30 min) antisera were pre-incubated for 1 hr at 23° C. with nanomolar amounts of either peptide SP-2, SP-3/4A or negative control peptide SP-7 (containing HTLV-I envelope amino acids 374–392). Ten microliters of antisera were then added to microtiter wells containing $5 \times 10^4$ HTLV-I-infected C91PL cells and $5 \times 10^4$ uninfected C8166 human T-cells in 90 μl of RPMI 1640 media containing 10% heat-inactivated fetal calf serum. Microtiter plates were incubated overnight at 37° C. in a humidified chamber with 5% $CO_2$. The microtiter wells were then evaluated for the presence of syncytia with an Olympus OM-2 inverted microscope at 200× magnification. Results were that peptide SP-2, but not SP-3/4A or SP-7, absorbed greater than 90% of the neutralizing antibodies from both #20 and 21 antisera in a dose dependent manner, as shown by the increased numbers of syncytia in wells containing antisera plus SP-2 peptide. Peptide SP-2 by itself did not induce syncytium formation with C8166 or C91PL cells (not shown). Results show that neutralizing antibodies in #20 and 21 antisera were directed against peptide SP-2. (See FIG. 5.)

Truncated peptides containing partial amino acid sequences of HTLV-I peptide SP-2 (envelope amino acids 86–107) were synthesized and used in absorption experiments as described above. Only peptides containing HTLV-I envelope amino acids 86–98, 88–98 and 90–98 could absorb neutralizing antibodies in goat antisera #20 and 21. Studies mapped the neutralizing site to HTLV-I envelope amino acids 90–98. (See Table 6.)

EXAMPLE 7

Mutational Analysis of Amino-Terminal HTLV-I Neutralizing Doman

To determine which amino acids within HTLV-I envelope amino acids 88–98 were required for absorption of neutralizing anti-peptide antibodies to HTLV-I, 11 peptides (2L1. to 2L1. 11) were synthesized in which sequential amino acids were each replaced by the amino acid alanine. These 11 mutated peptides, as well as peptide 2L-1 bearing the native HTLV-I sequence, were used to absorb neutralizing antibodies in three goat anti-SP-2 antisera (#20, 21 and 128), as described in Example 6.B. As shown in Table 7, peptides with alanine substitutions of asparagines in positions 91 and 93 (peptides 1.6 and 1.8) were not able to absorb neutralizing antibodies to HTLV-I in all 3 sera. Also, peptide 1.3 with an alanine substitution in position 90 was unable to absorb antibodies in sera #21 and 128, while peptide 1.5 (alanine in position 92) was unable to absorb neutralizing antibodies in serum #20. Results identified HTLV-I envelope amino acids #90 (K), #92 (P), #93 (N), and #95 (N) as being important for HTLV-I neutralization.

Depicted in FIG. 6 are the results of the same experiments summarized in Table 7 except that FIG. 6 shows numbers of HTLV-I induced syncytia obtained for each peptide absorption of antisera #20, 21 and 128. Results are representative of experiments performed 3 times with 20 and 21 antisera and twice with 128 antisera.

TABLE 6

| Amino Acid Sequence (aa 86–107) | Absorption of Neutralizing Antibodies to HTLV-I with SP-2 Peptides | Neutralizing Ab Absorbed |
|---|---|---|
| P H W T K K P N R N G G G Y Y S A S Y S D P (SEQ ID NO: 28) | | + |
| G G G Y Y S A S Y S D P (SEQ ID NO: 29) | | − |
| P H W T K K P N R N G G G (SEQ ID NO: 30) | | + |
| W T K K P N R N G G G | | + |
| K K P N R N G G G (SEQ ID NO: 45) | | + |
| K P N R N G G G (SEQ ID NO: 46) | | − to ± |

TABLE 7

HTLV-I Peptide Mutagenesis

| Peptide | | Amino Acid Sequence (aa 88–98) | Neutralizing Ab Absorbed (goat #) | | |
|---|---|---|---|---|---|
| | | | 20 | 21 | 128 |
| HTLV-I | 2L-1 | WTKKPNRNGGG | + | + | + |
| | 2L1.1 | ATKKPNRNGGG (SEQ ID NO: 31) | + | + | + |
| | 1.2 | WAKKPNRNGGG (SEQ ID NO: 32) | + | + | + |
| | 1.3 | WTAKPNRNGGG (SEQ ID NO: 33) | + | − | − |
| | 1.4 | WTKAPNRNGGG (SEQ ID NO: 34) | + | + | + |
| | 1.5 | WTKKANRNGGG (SEQ ID NO: 35) | − | + | + |
| | 1.6 | WTKKPARNGGG (SEQ ID NO: 36) | − | − | − |
| | 1.7 | WTKKPNANGGG (SEQ ID NO: 37) | + | + | + |
| | 1.8 | WTKKPNRAGGG (SEQ ID NO: 38) | − | − | − |
| | 1.9 | WTKKPNRNAGG (SEQ ID NO: 39) | ± | + | + |
| | 1.10 | WTKKPNRNGAG (SEQ ID NO: 40) | ± | + | + |
| | 1.11 | WTKKPNRNGGA (SEQ ID NO: 41) | ± | + | + |

1. Important amino acids are N (93) and N (95) for all three sera.
2. Other amino acids required for absorption are K (90) for #21 and #128 sera and P (92) for #20 serum.
3. G (96–98) play a lesser role in absorption of #20 serum.

EXAMPLE 8

Neutralization of HTLV-II with Anti-Peptide Antisera

Antisera were raised in 2 goats to a peptide with an amino acid sequence (amino acids 82– 97) of HTLV-II envelope that was homologous to the neutralizing region of HTLV-I envelope defined above. This HTLV-II peptide, designated DP-90, was coupled to tetanus toxoid, and conjugates were used to immunize goats #120 and 135. (See Table 8.) Sera from both of these goats (but not pre-immune sera), neutralized HTLV-II as determined in syncytium assays performed as described in Example 6.B., except that HTLV-II infected Mo-T cells were substituted for HTLV-I infected C91PL cells. Antisera to the HTLV-II peptide DP-90 did not neutralize HTLV-I, indicating that HTLV-II envelope amino acids 82–97 contained an HTLV-II type-specific neutralizing site.

TABLE 8

Type-Specific Neutralization of HTLV-II

| | HTLV-II peptide (aa 82–97) |
|---|---|
| DP-90 | PHWIKKPNRQGLGYYS(C) |

| | Neutralization[a] of | |
|---|---|---|
| Goat # | HTLV-I | HTLV-II |
| 120 | − | + (1/40)[b] |
| 135 | − | + (1/20) |

[a] Performed in syncytium inhibition assay
[b] Last serum dilution that inhibited by >90%.

EXAMPLE 9

Induction of Neutralizing Antibodies to HTLV-I with a Carrier and Free Synthetic Peptide Inoculum In previous studies (Palker et al, *J. Immunol.* 142:3612–3619, 1989; Hart et al, *J. Immunol.* 145:2677–2685. 1990), it was demonstrated that synthetic peptides containing a site recognized by T-helper cells and a (B-cell) neutralizing site of human immunodeficiency virus type-1 (HIV-1) could elicit neutralizing antibodies to HIV-1 isolates without the need for coupling the peptide to a carrier molecule, such as tetanus toxoid. In order to circumvent the need to couple HTLV-I peptides to a carrier molecule such as tetanus toxoid, a chimeric HTLV-I peptide containing HTLV-I envelope amino acids 183–209 synthesized amino-terminally to the HTLV-I envelope sequence 88–98 was made. HTLV-I envelope amino acids 183–209 contain a site recognized by murine T.helper cells (amino acids 190–209, Kurata et al, *J. Immunol.* 143:2024–2030, 1989), sites recognized by neutralizing monoclonal antibody 0.5 alpha (amino acids 186–195, Ralston et al, *J. Biol. Chem.* 264:16343–16346, 1989) and a neutralizing murine monoclonal antibody (amino acids 190–199, Tanaka et al, *J. Immunol.* 147:354–360), as well as a site (amino acids 196–209) recognized by CD4+, human cytotoxic T-cells (Jacobson et al, *J. Immunol.* 146:1155–1162, 1991). (See FIG. 6.) When used to immunize two goats, antisera were obtained that neutralized HTLV-I (titer=1/20). Neutralizing antibodies could be absorbed with peptide SP-2 (amino acids 86–107) but not by peptide SP-3/4A (amino acids 176–209), indicating that this chimeric peptide could induce neutralizing antibodies to HTLV-I without the need for coupling to a carrier molecule. Moreover, all neutralizing antibodies to HTLV-I elicited by this peptide were directed against the neutralizing domain described above, and not against other previously defined neutralizing sites contained within this peptide.

The foregoing invention has been described in some detail by way of examples for purposes of clarity and understanding. It will be obvious to those skilled in the art from a reading of the disclosure that a vaccine for HTLV-I can further comprise at least one synthetic peptide corresponding to a hydrophilic envelope region of the transmembrane protein of HTLV-I (advantageously, YAAQNRRGLDLLFWEQGGLC (amino acids 374–388 of gp21); CRFPNITNSHVPILQE (amino acids 399–415); CPILQERPPLENR (amino acids 411–422); CILRQLRHLPSRVRYPHYS (amino acids 462–480); or (C)RYPHYSLIKPESSL(amino acids 475–488)). It will also be obvious that various combinations in form and detail can be made without departing from the scope of the invention.

The entire contents of all documents cited hereinabove, are hereby incorporated by reference and relied upon.

What is claimed is:

1. A peptide having an amino acid sequence selected from the group consisting of (C) PHWTKKPNRNGGGYYSASYSDP (SEQ ID NO:3);

(C) LNTEPSQLPPTAPP (Y) (SEQ ID NO:4); and (C) LLPHSNLDHILEPSIPWKSK (Y) (SEQ ID NO:6).

2. A peptide having an amino acid sequence selected from the group consisting of SSYHSSPCSPTQPVC (SEQ ID NO:15);

CTWNLDLNSLTTDQRLHPPC (SEQ ID NO:16);
HWIKKPNRQGLGYYSPSYNDPC (SEQ ID NO:17);
(C)SSPSWKFHSDVNFTQE (SEQ ID NO:18);
(C) SEPTQPPPTSPPLVHDSDLEH (SEQ ID NO:19);
and (C)SLAPVPPPATRRRR (SEQ ID N0:20).

3. A peptide having the amino acid sequence PHWIKKPNRQGLGYYS (C) (SEQ ID NO: 14).

4. A peptide having the amino acid sequence WTKKPNRNGGG (amino acids 4–14 of SEQ ID NO:3).

5. A chimeric peptide having the amino acid sequence LPPTAPPLLPHSNLDHILEPSIPWKSKWTKKPNRNGGG (SEQ ID NO:25).

6. A peptide having the sequence PHWIKKPNRQGLGYYS (amino acids 1–16 of SEQ ID NO:14).

7. A subsequence of a peptide having the amino acid sequence (C)PHWTKKPNRNGGGYYSASYSDP (SEQ ID NO:3) that includes the amino acid sequence WTKKPNRNGGG (amino acids 4–14 of SEQ ID NO:3).

8. A peptide having the amino acid sequence
(C)PHWTKKPNRNGGGYYSASYSDP (SEQ ID NO:3).

9. A peptide having the amino acid sequence
(C)LNTEPSQLPPTAPP(Y) (SEQ ID NO:4).

10. A peptide having the amino acid sequence LPPTAPPLLPHSNLDHILEPSIPWKSKWTKKPNRNGGG (SEQ ID NO:25), or portion thereof that includes at least the amino acids WTKKPNRNGGG (amino acids 28–38 of SEQ ID NO:25).

11. The peptide according to claim 1 wherein said peptide has the amino acid sequence (C)LLPHSNLDHILEPSIPWKSK(Y) (SEQ ID NO:6).

12. The peptide according to claim 1 wherein said peptide is bound to a solid support.

13. The peptide according to claim 2 wherein said peptide has the amino acid sequence
SSYHSSPCSPTQPVC (SEQ ID NO:15).

14. The peptide according to claim 2 wherein said peptide has the amino acid sequence
CTWNLDLNSLTTDQRLHPPC (SEQ ID NO:16).

15. The peptide according to claim 2 wherein said peptide has the amino acid sequence
HWIKKPNRQGLGYYSPSYNDPC (SEQ ID NO:17).

16. The peptide according to claim 2 wherein said peptide has the amino acid sequence
(S)SSPSWKFHSDVNFTQE (SEQ ID NO:18).

17. The peptide according to claim 2 wherein said peptide has the amino acid sequence
(S)SEPTQPPPTSPPLVHDSDLEH (SEQ ID NO:19).

18. The peptide according to claim 2 wherein said peptide has the amino acid sequence
(C)SLAPVPPPATRRRR (SEQ ID NO:20).

19. The peptide according to claim 12 wherein said peptide is bound to a solid support.

20. The peptide according to claim 3 wherein said peptide is bound to a solid support.

21. The peptide according to claim 4 wherein said peptide is bound to a solid support.

22. The peptide according to claim 6 wherein said peptide is bound to a solid support.

23. A composition comprising the peptide according to claim 7 and a pharmaceutically acceptable carrier.

24. The peptide according to claim 7 wherein said peptide is bound to a solid support.

25. A composition comprising the peptide of claim 10 and a pharmaceutically acceptable carrier.

26. The peptide of claim 10 wherein said peptide is bound to a solid support.

\* \* \* \* \*